United States Patent [19]

Seagrave, Jr.

[11] Patent Number: 5,234,435
[45] Date of Patent: Aug. 10, 1993

[54] SURGICAL METHOD AND APPARATUS

[76] Inventor: Richard A. Seagrave, Jr., 1256 Sugar Hill Pl., Springfield, Mo. 65809

[21] Appl. No.: 665,953

[22] Filed: Mar. 8, 1991

[51] Int. Cl.$^5$ .............................................. A61F 5/04
[52] U.S. Cl. ...................................... 606/103; 606/86; 606/88; 623/13
[58] Field of Search ...................... 606/80, 86, 87, 88, 606/96, 99, 103, 104; 623/13

[56] References Cited

U.S. PATENT DOCUMENTS

| | | | |
|---|---|---|---|
| 4,450,835 | 5/1984 | Asnis et al. | 606/96 X |
| 4,712,452 | 12/1987 | Daniel et al. | 606/96 |
| 4,739,751 | 4/1988 | Sapega et al. | 606/88 X |
| 4,772,286 | 9/1988 | Goble et al. | 623/13 |
| 4,787,377 | 11/1988 | Laboureau | 606/96 X |
| 4,823,780 | 4/1989 | Odensten et al. | 606/96 |
| 4,828,562 | 5/1989 | Kenna | 623/13 |
| 4,927,421 | 5/1990 | Gobel et al. | 606/96 X |
| 4,946,462 | 8/1990 | Watanabe | 606/103 X |
| 4,950,271 | 8/1990 | Lewis et al. | 606/99 X |

Primary Examiner—Robert A. Hafer
Assistant Examiner—Sam Rimell
Attorney, Agent, or Firm—Beveridge, DeGrandi, Weilacher & Young

[57] ABSTRACT

Arthroscopic knee surgery is performed without a thigh incision by cutting a plug-receiving bore in the tibia, cutting a bore through the femur with a cannulated drill bit which is inserted through the tibial bore at an acute angle, and passing a wire in a proximal direction through the cannulated bit until it punctures and exits the thigh. The wire has a bend which is kept straight while it is in the cannulated bit but, upon exiting the bit, the wire's resilience restores the bend to direct the puncturing tip of the wire anteriorly toward the surface of the thigh. During the procedure, the proximal and distal ends of the wire are available to facilitate the movement of elements including a replacement graft to and from the site via the tibial bore.

31 Claims, 3 Drawing Sheets

SURGICAL METHOD AND APPARATUS

BACKGROUND OF THE INVENTION

This invention relates to a method and apparatus for performing surgical procedures. It is particularly adapted to arthroscopic surgery for reconstruction of anterior cruciate ligaments, but certain features may be applicable to nonarthroscopic surgery of the knee or arthroscopic surgery of other sites such as the shoulder.

Various techniques have evolved for anterior cruciate ligament surgery. Most but not all procedures involve the forming of an incision in the thigh, and the insertion of a drill through the thigh incision to drill a hole through the femur. Similarly, a lower incision is made to permit the drilling of a hole in the proximal end of the tibia. The replacement graft, either natural or artificial, is connected to a passing member which is threaded through the femoral and tibial holes, and the graft is pulled into position where it is properly fixed.

In an alternative type of anterior cruciate ligament surgery developed by Thomas D. Rosenberg, all drilling is done through an incision below the knee, including the drilling of a blind hole in the femur. A patellar tendon graft, held by a bone grasper, is inserted first through the tibial hole and then into the femoral hole. The proximal end of the graft is fixed to the femur by a fixation screw.

In a technique disclosed by Watanabe's U.S. Pat. No. 4,946,462, anterior cruciate ligament reconstructive surgery is performed by forming an incision in the thigh, feeding a graft-engaging passing member up through holes in the tibia and femur, and through the thigh incision. The graft is connected to the passing member which is then pulled in a distal direction until it is at the desired position where it is fixed in place.

The present invention varies from the prior art in several respects which are believed to provide distinct advantages. Operative time is decreased. No anterior thigh incision is required. Graft-receiving bores in the tibia and femur do not have to be perfectly aligned. If it becomes necessary to remove a graft after it is initially positioned at the site, it is not necessary to rethread the graft-passing wire in order to reinsert the graft.

One feature of the invention involves the procedure and tools for forming the femoral hole and for positioning a graft-passing member so that it extends through the hole as to have a midportion extending through the joint, a proximal portion extending from and accessible above the thigh, and a distal portion below the knee. Thus, a graft can be moved into position, withdrawn, and then moved back into position without rethreading the graft-passing wire through the tibia and femur. The invention also involves a technique for puncturing tissue after drilling through a bone in a manner which provides directional movement of the puncturing device to control the location where it exits the body. Various other features involve a member which serves both as a drill bit and a wire-guiding member, an obturator which prevents matter from entering a bore in the drill bit, a stop member which is attachable to the passing wire and has dimensions which prevent it from entering the femoral hole, a rotary-bone cutting tool which is moved to and advanced at a femoral drilling site by tension on a guide wire, and a flexible container filled with radiopaque fluid which is passed to the surgical site by a guide wire to permit visualization of the shapes of bores formed for receiving the opposite ends of the graft. Most importantly, however, the wire is connectable to a replacement ligament so that the ligament may be moved in opposite directions to and from its desired site.

SUMMARY OF THE INVENTION

According to one aspect of the invention, surgery includes a step of placing a cannulated guide tube at a position where its outlet end is in the patient's body and its inlet end is outside the patient's body, a guide wire is moved in an insertion direction through the guide tube and beyond its outlet end until the guide wire punctures tissue and exits the patient's body, and the guide tube is removed from the patient's body. An element, preferably a replacement graft, is connected to the guide wire which is then pulled in the insertion direction to move the element to the surgical site.

The method described in the preceding paragraph is preferably performed in a manner so that both ends of the guide wire are outside the patient's body when the element is at the surgical site, thus making it possible to withdraw the element from the surgical site in a direction which is opposite to the insertion direction. In order to control the direction travelled by the guide wire while puncturing tissue, it is preferred that the guide wire be provided with a resilient leading end portion with a bend formed therein. The guide tube has a shape which keeps the bend straight until it exits the guide tube so that, upon exiting the guide tube, the wire will resume its bent shape to affect the direction it travels.

Also it is preferred that the guide tube be provided with cutting means at its outlet end so that it is operable as a rotary drill bit to cut a bore in a bone before the guide wire is moved through it. Such a drill bit advantageously is provided with an obturator which permits material from entering its bore during drilling. The obturator is removed before the wire is passed through the bore.

Further, the invention preferably involves the use of a stop member which is connected to the guide wire and has dimensions which prevent it from passing through a bore in a bone, thus permitting the surgeon to conduct an isometry test to determine the suitability of a selected fixation site.

With particular regard to anterior cruciate ligament reconstructive surgery, another aspect of the invention involves the procedure whereby a graft is positioned by inserting a wire through the tibia and then through the femur, pushing the wire to force it beyond the femur and puncture the thigh so that a proximal portion of the wire is exposed and accessible, connecting a replacement ligament to the wire distally of the tibia, pulling the proximal portion of the wire to pull the replacement ligament first through the tibia and then into the femur, and fixing the replacing ligament to the tibia and to the femur. Preferably, this aspect of the invention also involves the use of a cannulated drill bit which is rotated to cut through the femur, and the insertion of the wire through the bore of the cannulated drill bit, at which time the drill bit serves as a guide tube. The drill bit has a smaller diameter than the tibial bore and, during drilling it extends through the tibial bore at an acute angle thereto. Also, it is preferred to perform the method with a resilient wire provided with a bend which is kept straight by the guide tube until it exits the guide tube and enters the tissue. A cutting tool is placed on the wire, and it is rotated while advancing it into the femur to form a recess for receiving a bone plug of a replacement graft.

The invention also involves a kit of instruments for performing anterior cruciate ligament reconstructive surgery. The kit includes a cannulated drilling and wire-guiding means with cutting means at its leading end and a longitudinal bore. A removable obturator is located in the bore to prevent matter from entering the bore while drilling. A wire is insertable in the bore and is movable through the drilling and wire-guiding means, and a stop means is affixable on the wire to stop lengthwise movement of the wire through a bore formed in a bone by the drilling and wire-guiding means. These and other features of the invention will be understood by the following description of a preferred embodiment.

DETAILED DESCRIPTION

The present invention is used in connection with known surgical techniques using conventional instruments. Normal preoperative procedures are followed. The patient is positioned on a fracture table in a way that provides good access to the medial and lateral aspects of the knee and the knee can be easily flexed 100 degrees. Conventional diagnostic arthroscopy and limited notchplasty are performed. An anterior incision is made over the patellar tendon, and the middle third of the patellar tendon is removed with bone plugs 2 cm long for use as the replacement graft. Holes are drilled through the bone plugs, and sutures are threaded through these holes to provide a means for handling the graft.

A hole 2 is reamed in the tibia 4 with a reamer to an appropriate size which is usually about 10 cm. The reamer is rotated by a flexible drive shaft which is guided by a precisely positioned tibial guide pin. As is known in the art, the surgeon should consider coalignment in selecting the location and orientation angle of the tibial bore. In most cases, it is started just medial to the patellar tendon, and about two cm distal to the joint line.

Figure 1:
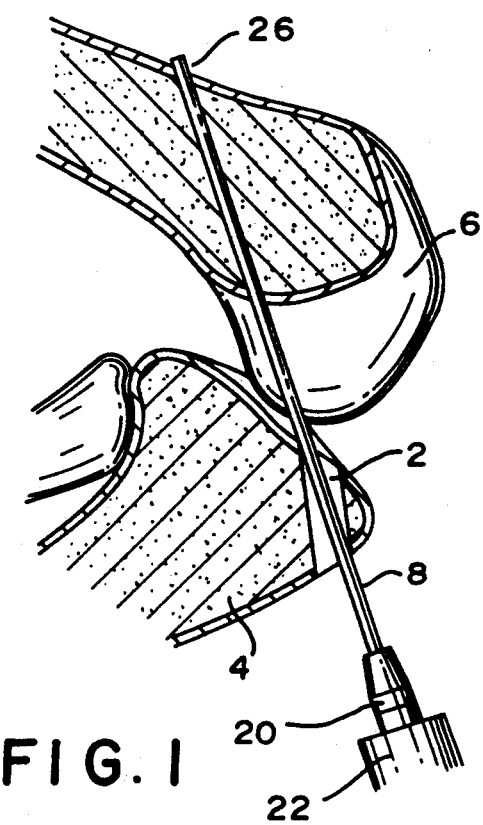
FIG. 1 is a lateral view of a knee joint as seen at the conclusion of drilling a bore through the femur.
Figure 3:
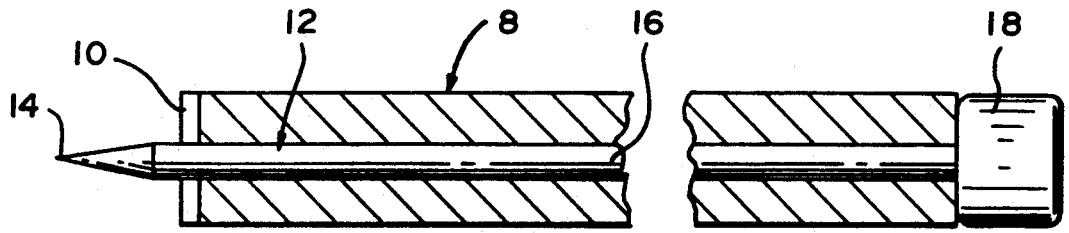
FIG. 3 is a broken view, partially in section, of the cannulated member which serves as a drill bit in FIG. 1 and a guide tube in FIG. 2. An obturator is shown in the bore of the cannulated member.

Having completed the foregoing known procedures, the surgeon then drills a wire-receiving bore through the femur 6 as shown in FIG. 1. The drill bit 8 is subsequently used as a guide tube, so it is referred to herein both as a bit member and as a guide member. As shown in FIG. 3, it has a tubular body with cutting teeth 10 at its leading end. It has a diameter of about 3 mm, and a length of about 20 cm. As shown in FIG. 3, it is provided with an obturator 12 which has a pointed leading end 14 which assists the bit in maintaining its position during the initial stages of drilling. A knob 18 is provided at the rear end of the obturator shaft 16. The shaft 16 of the obturator fills the bore of the bit to prevent material from entering the bit during drilling. Threads, an interference fit or other means may be used to fix the obturator 12 in the member 8.

The surgeon attaches the bit 8 to the chuck 20 of a conventional surgical drill 22 and, with the help of an image intensifier if available, the bit is introduced through the tibial bore 2 at an acute angle to its axis, and to a position on the femur 6 which is as close as possible to the over-the-top position. The bit is rotated and advanced longitudinally until it cuts through the femur 6 and obliquely exits the anterolateral cortex. Normally, the knee will be flexed approximately 100 degrees if coalignment was considered when making the tibial bore.

Figure 2:
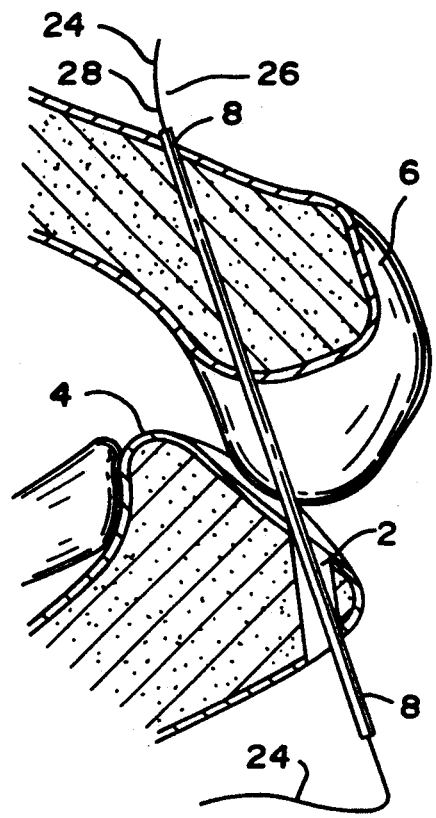
FIG. 2 shows the insertion of a wire through a guide tube when the leading end of the wire punctures the patient's thigh.

The drill chuck 20 is disconnected from the bit 8 and the obturator 12 is removed from the bore of the bit. At this point, the member 8 commences to serve as a guide tube. As shown in FIG. 2, a guide wire 24 is inserted through the guide tube 8 so that it passes first through the tibial bore 2, then through the femoral bore, and then into the previously undisturbed flesh of the thigh 26 anteriorly of the femur.

Figure 4:
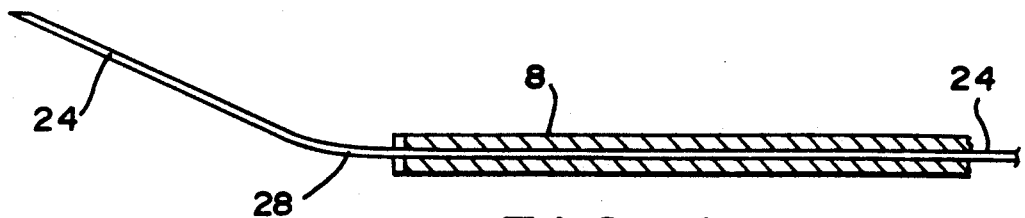
FIG. 4 is an enlarged view of the leading end portion of the cannulated member, also showing the configuration of the wire after it exits the leading end of the cannulated member.

The portion of the wire 24 shown in FIG. 2 is relatively stiff and resilient stainless steel having a diameter of about 0.8 mm. As shown best in FIG. 4, its leading end portion has a permanent bend 28 when the wire is in a relaxed state, not subjected to external forces. Due to the relative inflexibility of the guide tube 8, the bend 28 will be substantially straight as it moves longitudinally within the tube 8. However, upon exiting the guide tube 8, the wire 24 resumes its bent shape. Due to this characteristic, it is possible to control the direction of travel of the wire 24 as it punctures the thigh 26. As shown in FIG. 2, the wire is oriented so that the wire will surface quickly to reduce the distance it travels in a proximal direction, thus preventing the wire from exiting in the area where the surgeon normally attaches a tourniquet when performing surgery of this nature. This feature is also important because it permits the surgeon to drill a very oblique bore in the femur while assuring the availability of sufficient room in the thigh to retrieve the guide wire.

After the leading end of the wire 24 has punctured and exited the thigh, the guide tube 8 is removed. The wire remains in position, and the pathway it establishes will not be lost until the graft is seated and secured in its final position. The surgeon has an exposed proximal portion which is accessible above the knee, and an exposed distal portion which is accessible below the knee.

As will be described subsequently, the presence of this wire makes it possible to control the movements of a variety of elements used in the surgical procedure.

Preferably, the proximal 25 cm. of the wire 24 has the stiffness and resilience mentioned above. Thereafter, the wire has a length of about 130 cm. formed of two flexible strands which are twisted together. About 65 cm. from the proximal end of the wire, the twisted strands are spread apart to provide a transversely open loop or eye for receiving the sutures of the replacement graft as will be described below in this specification.

Figure 5:
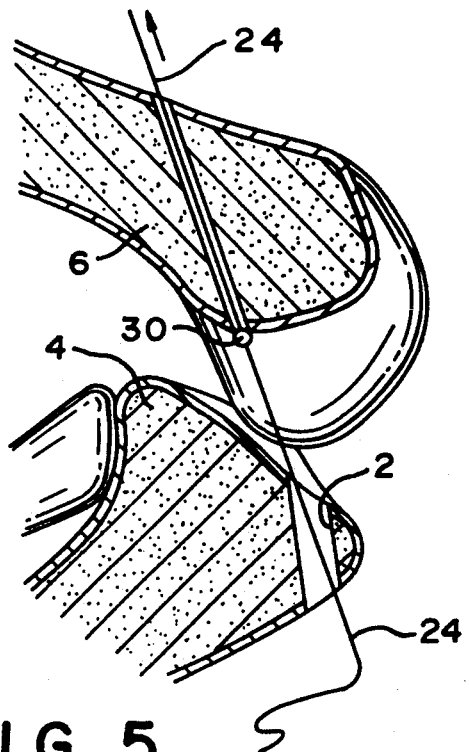
FIG. 5 is a lateral view of the knee joint during an isometry test which is performed to test the suitability of the fixation site on the femur.

Before forming a graft-receiving recess in the femur 6, it is desirable to perform an isometry test which, if successful, will confirm the suitability of the fixation site established on the femur. Ideally, there is very little variation in the distance between the femoral and tibial attachments sites while the joint is flexed, and the purpose of the isometry test is to confirm this condition. It is performed by attaching a small spherical enlargement 30 to the wire using a set screw. This enlargement or "stop" is shown in FIG. 5, where it will be seen that it has been drawn by the wire 24 to a position where it abuts the femur 6 at the distal end of the femoral bore. The knee is flexed, and the surgeon observes the extent of relative movement between the wire 24 and the distal end of the tibial bore 2. If this movement is excessive, another site may be selected and the procedure shown in FIGS. 1 and 2 repeated. Such repetition will generally be unnecessary if the surgeon tends to select a posterior attachment site on the femur.

Figure 6:
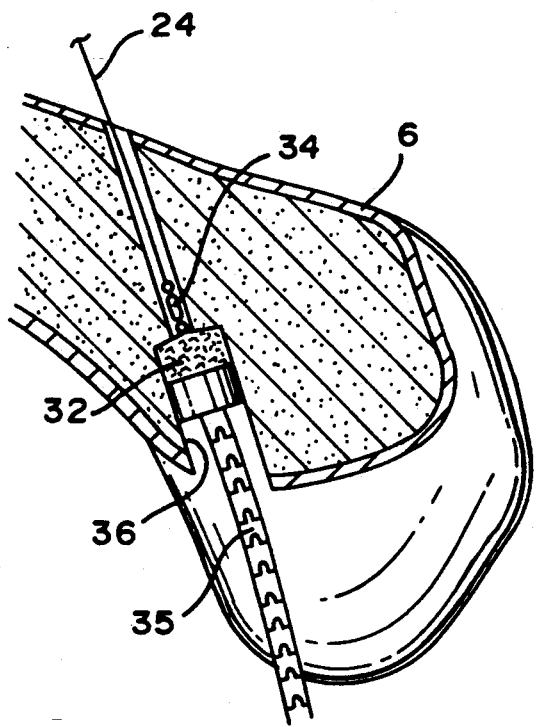
FIG. 6 shows the reaming of a countersunk recess in the femur suitable for receiving the plug of a graft.

A recess is now formed in the femur for receiving the femoral plug of the replacement graft. As illustrated in FIG. 6, this recess is a counterbore formed by a reamer 32 which is connected to the wire by a swivel 34. The reamer is driven by a motor connected to flexible drive shaft 35. The proximal end of the wire 24 is pulled to advance the rotating reamer 32 into the femur until the recess 36 is reamed to a suitable depth, normally about two cm. The swivel 34 allows the reamer head to twist freely, and the flexible drive shaft eliminates the necessity for perfect coalignment of the tibial and femoral bores.

Figure 7:
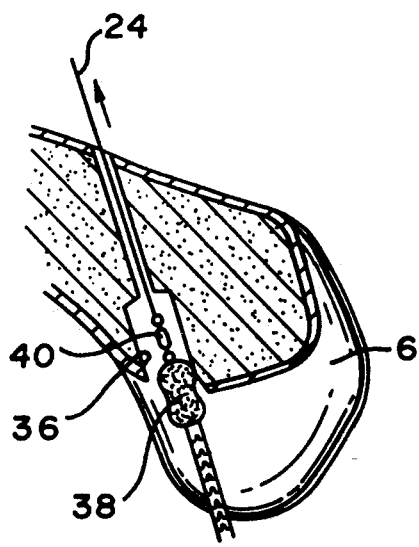
FIG. 7 illustrates the use of a chamfering tool for rounding the edges at the entrance end of the femoral recess.
Figure 9:
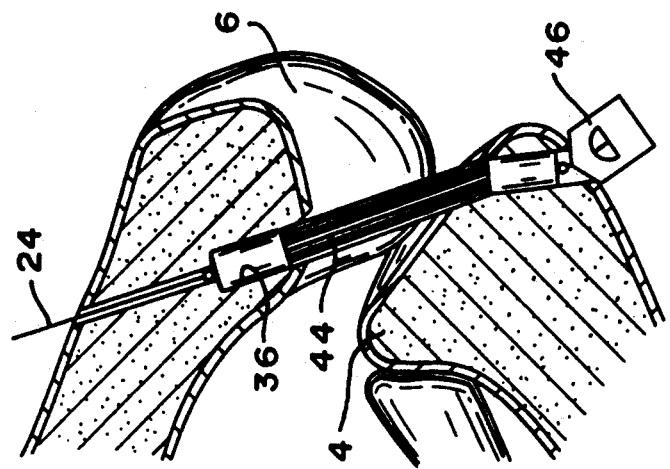
FIG. 9 illustrates the performance of a tension check to determine the tension in a graft for the particular patient.

The reamer 32 is then removed and detached from the wire 24. As shown in FIG. 7, a chamfering tool 38 with a burred exterior surface is connected to the distal end of the wire 24 by a swivel 40. The exposed proximal section of the wire is pulled to pass the chamfering tool 38 into the tibial bore 2 and femoral recess 36. This provides a rounded entrance to the femoral recess 36 to prevent impingement of the replacement graft at this edge. The chamfering tool also provides a rounded edge in the tibial bore 2 as can be seen in FIG. 9. While using the chamfering tool, smoothing of the notchplasty can also be accomplished by flexing and extending the knee.

Figure 8:
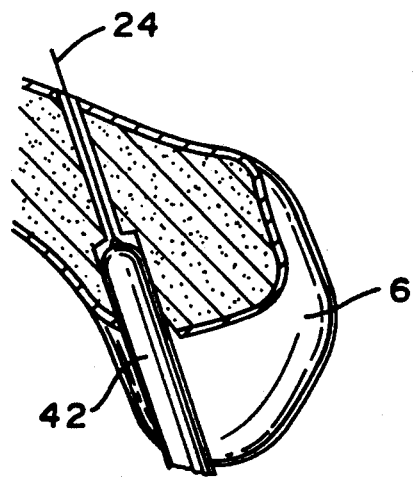
FIG. 8 shows the use of a radiopaque device for ascertaining the shape of the plug-receiving bores.

It is desirable to test the notchplasty and chamfering visually as shown in FIG. 8, using a flexible container 42 filled with a radiopaque fluid such as Radiografin. This member 42 is attached to a midportion of the wire 24 and pulled into positions where it occupies the femoral recess 36 and the tibial bore 2. The container is conformable to the bone surfaces in the femoral recess and tibial bore to permit radiological evaluation of the shapes of the recess and bore. By viewing the image intensifier, the surgeon is able to confirm that the recess and bore have been properly reamed and chamfered, and that notchplasty has been suitably performed.

As shown in FIG. 9, a trial ligament 44 may be attached to the wire 24 and drawn into position for performance of a tension check. While pulling on the proximal portion of the wire 24 to hold the femoral plug of the trial ligament securely in its respective recess 36, a tension gauge 46 is attached to the distal end of the trial ligament 44. The joint is flexed while observing the scale on the tension gauge 46. Excessive variations in tension may necessitate modifications.

Figure 10:
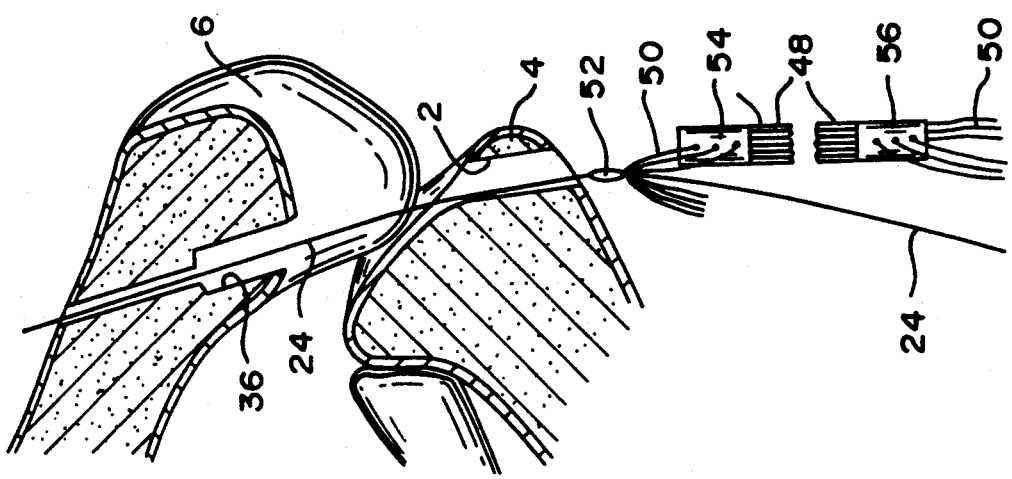
FIG. 10 illustrates the initial step of passing the graft into the knee joint.

After confirming that the site is ready for receiving the graft, the patellar graft 48 is connected to the passing wire as shown in FIG. 10 by inserting the stay sutures 50 through the central loop or eye 52 in the wire. The proximal end of the wire is pulled until the femoral plug 54 of the graft abuts the blind end of the femoral recess 36, and the tibial plug 56 of the graft is positioned in the tibial bore 2. Due to the small diameter of the guide wire 24, it may remain in position. If adjustments are required, the distal end of the wire 24 can be pulled to withdraw the ligament 48.

The bone plugs of the graft are then fixed in their respective recesses using known techniques such as staples, screws, or K-wire-guided cannulated fixation screws.

Figure 11:
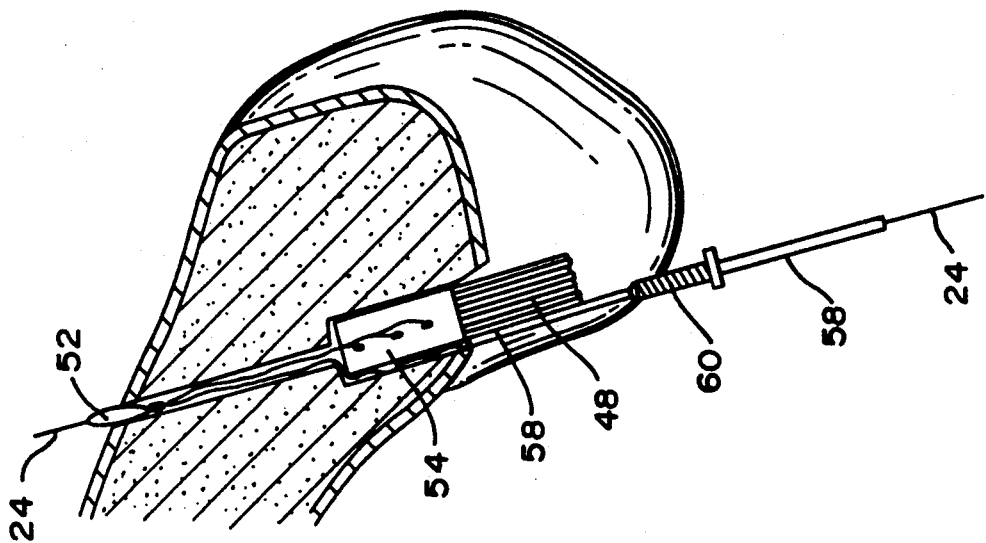
FIG. 11 shows the step of fixing the femoral plug of the graft in the femoral graft-receiving recess by use of a cannulated fixation screw.

If the guide wire 24 remains in position, it may be used to guide a cannulated fixation screw to the femur as shown in FIG. 11. Before doing this, the guide wire is removed from the tibial bore. A screw-guiding tube 58 is telescoped over the wire to increase its stiffness and, using a known type of cannulated fixation screw 60 and driver, the bone plug of the graft is securely anchored in the femur. At this point, with the graft 48 fully positioned and fixed, the wire 24 may be removed by pulling on its proximal end.

By utilization of the invention, the only required incisions are the arthroscopic portals and the anterior harvesting incision. Operative time is decreased. The technique is reproducible and it appropriately provides bore locations and bore angles which adhere to the principles of coalignment. The invention permits convenient testing of ligament tension and inspection of the bore chamfering and notchplasty. The graft positioning and graft fixation are convenient, and the graft fixation is secure.

The invention is particularly suited to arthroscopic knee surgery because it avoids the requirement for a thigh incision, it facilitates movement of tools and reconstructive elements to and from the site, and it facilitates the utilization of a posterior fixation site on the femur. However, it is believed that certain aspects of the invention may be useful in other types of surgery, for example the feature whereby a resilient wire resumes a prebent shape when it exits the leading end of a guide tube within the patient's body.

The invention is susceptible to numerous modifications. The graft may have natural or artificial ligaments. The wire may be formed of multiple strands or a single strand which is metallic or nonmetallic, and its physical characteristics may be uniform or variable along its length. Cannulated reamers or chamfering tools may travel along the wire. In such situations, a cannulated guide sleeve with an external guide surface may be placed on the wire to increase its stiffness.

In view of the possible diverse applications of the principles of this invention, it is emphasized that the invention is not limited solely to the disclosed embodiment, but is embracing of variations thereto and modifications thereof which fall within the spirit of the following claims.

I claim:

1. A method of performing anterior cruciate reconstructive surgery on a patient having a thigh and a knee joint which connects a femur to a tibia, said method including the following steps:
   (a) cutting a tibial bore through the tibia;
   (b) cutting a femoral bore through the femur;
   (c) inserting a wire through the tibial bore and then through the femoral bore,
   (d) forcing the wire beyond the femur and through the thigh until the wire has an exposed proximal portion which is accessible above the thigh,
   (e) connecting a replacement ligament to the wire distally of the tibia,
   (f) pulling the proximal portion of the wire to pull the replacement ligament first through the tibia and then into the femur, and
   (g) fixing the replacement ligament to the tibia and to the femur.

2. A method according to claim 1 in which the femoral bore is cut through the femur with a drill bit which (i) extends through the tibial bore, (ii) has a smaller diameter than the tibial bore, and (iii) is oriented at an acute angle to the tibial bore.

3. A method according to claim 1 in which the following steps are performed prior to step (c):
   inserting a cannulated guide tube first through the tibial bore and then through the femoral bore, said cannulated guide tube having a bore,
   said step of inserting a wire being performed by passing the wire through the bore of the cannulated guide tube.

4. A method according to claim 3 in which the cannulated guide tube is a cannulated drill bit which is rotated to cut the femoral bore.

5. A method according to claim 3 wherein the cannulated drill bit has an obturator which prevents material from entering the drill bit bore during drilling, said method including the step of removing the obturator from the drill bit bore before the wire is passed through it.

6. A method according to claim 1 wherein the wire is resilient and has a leading end portion with a bend therein when the wire is in a relaxed state;
   said step of inserting the wire through the femur being performed in a guide tube which keeps the bend straight until it exits the guide tube, said wire upon exiting the guide tube resuming its shape including said bend to affect the direction it punctures the thigh and to reduce the distance it travels before it exits the thigh.

7. A method according to claim 1 including the performance of an isometry test between step (d) and (e), said isometry test being performed by attaching a stop to the wire, pulling the exposed portion of the wire until the stop engages the femur, and conducting an isometry test by moving the tibia relative to the femur through a range of motion while observing the distance the tibia moves relative to the wire.

8. A method according to claim 1 including the cutting of a recess in the femur between steps (d) and (e) by
   placing a cutting tool on the wire; and,
   cutting said recess by rotating said cutting tool while advancing it into the femur.

9. A method according to claim 8 in which s cannulated guide sleeve with an external guide surface is placed on the wire, said cutting tool being cannulated and being guided on said wire by said guide sleeve during said cutting step.

10. A method according to claim 8 in which the wire is attached to the cutting tool and the exposed proximal portion of the wire is pulled to pull the cutting tool into the femur.

11. A method according to claim 10 in which the step of fixing the replacement ligament includes the following steps:
    placing a cannulated fixation screw on said wire, and guiding said screw on said wire while rotating said screw to screw it into said femur.

12. A method according to claim 11 wherein a cannulated guide sleeve is placed on said wire, said cannulated guide sleeve having an external surface which guides and supports the fixation screw on the wire.

13. A surgical method for positioning an element at a surgical site in the body of a patient, said method involving the use of a guide wire and a cannulated guide tube with inlet and outlet ends, said method including the following steps:
    creating a hole in the patient's body,
    inserting the outlet end of the cannulated guide tube in the patient's body.
    moving the guide wire in an insertion direction through the guide tube and then beyond its outlet end until the guide wire punctures tissue and exits the patient's body,
    removing the guide tube from the patient's body, connecting an element to the guide wire, and pulling the guide wire in said insertion direction to move the element to the surgical site.

14. A method according to claim 13 in which the guide wire has two ends which both are outside the patient's body when the element is at the surgical site, whereby the element can be withdrawn from the surgical site in a direction which is opposite to the insertion direction.

15. A method according to claim 13 in which the wire has a resilient leading end portion with a bend therein when the wire is in a relaxed state,
    said guide tube having a shape which keeps the bend straight until it exits the guide tube, said wire upon exiting the guide tube resuming its shape including said bend to affect the direction it travels.

16. A method according to claim 13 wherein the step of connecting an element to the guide wire is performed by connecting a replacement ligament to the guide wire.

17. A method according to claim 13 wherein the cannulated guide tube is a drill bit with cutting means at its outlet end, said method including the step of rotating said guide tube to cut a bore in a bone before moving said guide wire through the guide tube.

18. A method according to claim 17 wherein the cannulated drill bit has an obturator which prevents material from entering the bore during cutting of the bore, said method including the step of removing the obturator from the bore before the wire is passed through the bore.

19. A method according to claim 17 wherein the stop of connecting an element to the guide wire is performed by connecting, to the guide wire, a stop member having dimensions which prevent it from passing through said bore in the bone.

20. A method according to claim 13 including the step of placing a cannulated fixation screw on the guide wire, and moving the fixation screw along the guide wire to the surgical site.

21. A method according to claim 13 wherein the step of connecting an element to the guide wire is performed by connecting, to the guide wire, a rotary bone-cutting tool.

22. A method according to claim 13 wherein the step of connecting an element to the guide wire is performed by connecting, to the guide wire, a flexible radiopaque element which is conformable to bone surfaces at the surgical site.

23. A method of performing anterior cruciate ligament reconstructive surgery on a patient whose body has a thigh and a knee joint which connects a femur to a tibia, said method including the following steps:
    forming bores in the tibia and femur;
    attaching a replacement ligament to a midportion of a wire which has proximal and distal portions extending in opposite directions from said midportion; said wire in a proximal direction to carrying a replacement ligament to a position where it extends from the tibia to the femur, to an operative position where, simultaneously, (a) said midportion thereof is in said bores, (b) said proximal portion is exposed and extends out from the patient's body, and (c) said distal portion is exposed and extends out from the patient's body.

24. A method according to claim 23, also including the step of connecting a cutting tool to said wire, and rotating said cutting tool to cut a graft-receiving recess in a distal surface of the femur.

25. A method according to claim 23, also including the step of attaching a flexible radiopaque body to the wire, and moving the wire in a proximal direction to carry said radiopaque body into the recess, said radiopaque body being conformable to the shape of the recess to permit radiological evaluation of the shape of the recess.

26. A method of performing anterior cruciate ligament reconstructive surgery on a patient whose body has a thigh and a knee joint which connects a femur to a tibia, said method including the following steps:
    forming bores in the tibia and femur, inserting a wire through said bores; said wire having an operative position where, simultaneously, (a) a midportion thereof extends through said bores, (b) an exposed proximal portion thereof extends out from the patient's body, and (3) an exposed distal portion thereof extends out from the patient's body; said midportion lying between the proximal portion and the distal portion;
    providing an enlargement on the wire, moving the wire in a proximal direction until the enlargement engages against a distal surface of the femur, moving the knee joint through a range of motion while observing changes in the position of a wire relative to the tibia to determine the suitability of the location of the bore in the femur;
    attaching a replacement ligament to the wire;
    and, moving the wire in a proximal direction to carry the replacement ligament to a position where it extends from the tibia to the femur.

27. A kit of instruments for performing anterior cruciate ligament reconstructive surgery, comprising,
    a cannulated drilling and wire-guiding means having a longitudinal bore and an annular leading end provided with cutting means,
    obturator means located in said bore and obstructing said bore adjacent to said cutting means to prevent matter from entering said bore during a drilling procedure, said obturator means being removable from said bore,
    a wire which is insertable in said bore and is movable through said drilling and wire-guiding means, and
    stop means for providing a stop which is fixed on said wire to stop lengthwise movement of the wire through a bore which is formed in a bone, said stop means being larger diametrically than said drilling and wire-guiding means.

28. A kit of instruments according to claim 27 which also includes a cannulated tool-guiding sheath means having a bore which is larger than said wire so that said sheath means is capable of moving on said wire precisely to a surgical site and then guiding an element for longitudinal and rotary movement along said wire.

29. A kit of instruments according to claim 27 wherein the wire has a resilient leading end portion with a bend therein, said drilling and wire-guiding means having a shape which keeps the bend straight until it exits the drilling and wire-guiding means.

30. A method according to claim 2 wherein the wire is provided with an enlargement which is unable to pass through the femoral bore formed during step (b); and, between steps (d) and (e), the wire is moved in a proximal direction until said enlargement engages against a distal surface of the femur, moving the knee joint through a range of motion while observing changes in the position of the wire relative to the tibia to determine the suitability of the location of the femoral bore, and, after observing said changes and before step (f), cutting the femur to enlarge said femoral bore.

31. A method of performing surgery using a cannulated wire-guiding means with inlet and outlet ends, and a wire which has a resilient leading end portion provided with a bend having a bent shape, said method including the steps of placing the outlet end of the wire-guiding means at a surgical site, positioning the leading end portion of the wire in the wire-guiding means to straighten said bend, and moving the wire lengthwise in the wire-guiding means until the bend passes beyond the outlet end of the wire guiding means and resumes its bent shape to cause the leading end portion of the wire to move in a direction determined by the orientation of the bend.

* * * * *